United States Patent [19]
Woodburn et al.

[11] Patent Number: 6,022,526
[45] Date of Patent: Feb. 8, 2000

[54] USE OF TEXAPHYRINS IN DETECTION OF MELANIN AND MELANIN METABOLITES DIAGNOSTIC OF MELANOTIC MELANOMA

[75] Inventors: Kathryn W. Woodburn, Sunnyvale; Stuart W. Young, Portola Valley, both of Calif.

[73] Assignee: Pharmacyclics, Inc., Sunnyvale, Calif.

[21] Appl. No.: 08/903,099

[22] Filed: Jul. 30, 1997

[51] Int. Cl.⁷ .................................................. A61K 49/00
[52] U.S. Cl. ...................... 424/9.61; 424/1.11; 424/1.65; 424/9.1; 424/9.3; 424/9.6; 435/7.1; 435/7.23; 436/518; 436/64; 436/58
[58] Field of Search .................................. 424/1.11, 1.65, 424/9.1, 9.3, 9.6, 9.61; 435/7.1, 7.23; 436/518, 58, 64, 161

[56] References Cited

U.S. PATENT DOCUMENTS

| | | | |
|---|---|---|---|
| 4,749,559 | 6/1988 | Kebabian | 424/1.1 |
| 4,843,020 | 6/1989 | Woodford | 436/518 |
| 4,935,498 | 6/1990 | Sessler et al. | 534/15 |
| 5,021,236 | 6/1991 | Gries et al. | 424/9 |
| 5,252,720 | 10/1993 | Sessler et al. | 534/11 |
| 5,256,399 | 10/1993 | Sessler | 424/9 |
| 5,292,414 | 3/1994 | Sessler et al. | 204/157.5 |
| 5,310,539 | 5/1994 | Williams | 424/9 |
| 5,457,183 | 10/1995 | Sessler et al. | 534/11 |
| 5,559,207 | 9/1996 | Sessler et al. | 530/300 |
| 5,565,552 | 10/1996 | Magda et al. | 534/11 |
| 5,567,687 | 10/1996 | Magda et al. | 514/44 |
| 5,576,013 | 11/1996 | Williams et al. | 424/423 |
| 5,583,220 | 12/1996 | Sessler et al. | 540/472 |
| 5,587,371 | 12/1996 | Sessler et al. | 514/185 |
| 5,587,463 | 12/1996 | Sessler et al. | 534/15 |
| 5,591,422 | 1/1997 | Hemmi et al. | 424/9.362 |
| 5,594,136 | 1/1997 | Sessler et al. | 540/472 |
| 5,595,726 | 1/1997 | Magda et al. | 424/9.61 |
| 5,599,923 | 2/1997 | Sessler et al. | 540/145 |
| 5,599,928 | 2/1997 | Hemmi et al. | 540/474 |
| 5,601,802 | 2/1997 | Hemmi et al. | 424/9.363 |
| 5,607,924 | 3/1997 | Magda et al. | 514/44 |
| 5,622,946 | 4/1997 | Sessler et al. | 514/185 |

FOREIGN PATENT DOCUMENTS

| | | |
|---|---|---|
| WO90/10633 | 9/1990 | WIPO. |
| WO94/29316 | 12/1994 | WIPO. |
| WO95/10307 | 4/1995 | WIPO. |
| WO95/21845 | 8/1995 | WIPO. |
| WO95/24930 | 9/1995 | WIPO. |
| WO95/20981 | 10/1995 | WIPO. |
| WO95/29702 | 11/1995 | WIPO. |
| WO96/09315 | 3/1996 | WIPO. |
| WO96/38461 | 12/1996 | WIPO. |
| WO96/40253 | 12/1996 | WIPO. |
| WO 97/26915 | 7/1997 | WIPO. |
| WO 97/35617 | 10/1997 | WIPO. |

OTHER PUBLICATIONS

Anderson, et al., "The Optics of Human Skin," *J. of Investigative Dermatology*, 77(1):13–19, 1981.

Associated Regional and University Pathologists, Inc., "Melanin, Urine," Internet: http://www.arup–lab.com/ug/ugar1399.htm, updated Apr. 1, 1997.

Atlas, et al., "Human Malignant Melanomas with Varying Degrees of Melanin Content in Nude Mice: MR Imaging, Histopathology, and Electron Paramagnetic Resonance," *Journal of Computer Assisted Tomography*, 14(4):547–554, 1990.

Ball, et al., "Surgical Management of Malignant Melanoma," *British Medical Bulletin*, 51(3):584–608, 1995.

Biolo, et al., "Photodynamic Therapy of B16 Pigmented Melanoma with Liposome–Delivered Si(IV)–Naphthalocyanine," *Photochem. And Photobiol.*, 59(3):362–365, 1994.

Borovansky, J., "Properties of melanosomes and their exploitation in the diagnosis and treatment of melanoma," *Melanoma Research*, 3:181–186, 1993.

Brown, et al., "New Light on Cancer Therapy," *Chemistry in Britain*, pp. 955–958, 1993.

Cochran, et al., "Melanocytic Tumors: A Guide to Diagnosis," *Evaluative Techniques for Melanocytic Tumors*, 298–299, Sep., 1996.

Dougherty, T.J., "Photoradiation Therapy for Cutaneous and Subcutaneous Malignancies," *The Journal of Investigative Dermatology*, 77:122–124, 1981.

Dougherty, T.J., "Photosensitizers: Therapy and Detection of Malignant Tumors," *Photochemistry and Photobiology*, 45:879–889, 1987.

Ehrenberg, et al., "The Binding and Photosensitization Effects of Tetrabenzoporphyrins and Texaphyrin in Bacterial Cells," *Lasers in Medical Science*, 8:197–203, 1993.

Favilla, et al., "Photodynamic therapy: a 5–year study of its effectiveness in the treatment of posterior uveal melanoma, and evaluation of haematoporphyrin uptake and photocytotoxicity of melanoma cells in tissue culture," *Melanoma Research*, 5(5):355–364, Oct., 1995. (abstract only).

Haylett, et al., "Pharmacokinetic and therapeutic outcome in melanoma cells of the administration of symmetric and asymmetric cationic photosensitizers," *Cancer Letters*, 88:191–199, 1995.

Horstman, Judith, "Study to examine skin cancer drug activated by light," *Stanford University Campus Report*, Mar. 1996.

(List continued on next page.)

*Primary Examiner*—Sheela Huff
*Attorney, Agent, or Firm*—Aktin, Gump, Strauss Hauer & Feld L.L.P.

[57] ABSTRACT

Melanotic melanoma tumor or cells, melanin, or melanin metabolites are detected, identified, and localized when bound to texaphyrins or texaphyrin metal complexes. The present invention provides texaphyrins and texaphyrin metal complexes as reagents for in vivo or in vitro detection for melanin or melanin metabolites predictive of the presence of melanotic melanoma.

18 Claims, No Drawings

OTHER PUBLICATIONS

Hungerford, J.L., "Management of Ocular Melanoma," *British Medical Bulletin*, 51:694–716, 1995.

Jimbow, et al., "Melanin Pigments and Melanosomal Proteins as Differentiation Markers Unique to Normal and Neoplastic Malenocytes," *The Journal of Investigative Dermatology*, 259S–268S, 1993.

Kimura, et al., Macrocyclic Polyamines as Biological Cation and Anion Complexones—An Application to Calculi Dissolution, *Topics in Current Chemistry, 128, Biomimetic and Bioorganic Chemistry*, VII+265P, Springer, Verlag, Berlin, West Germany, pp. 113–141, 1985.

König, et al., "PDT of Tumor–bearing Mice Using Liposome Delivered Texaphyrins," Photodynamic Therapy & Biomedical Laser Applications, Spinelli, et al., Elsevier Science Publishers, 1992.

König, et al. "Photodynamic Activity of Liposome–Delivered Cd–Texaphyrin Using Tumor–Bearing Nude Mice," *Lasers in Surgery and Medicine*, 13:522–527, 1993.

Leff, D.N., "Texas 'Son–of–Porphyrin' Molecule Lassos Europium to Kill Drug Resistance Gene," *BioWorld Today*, 5:1–3, 1994.

Leunig, et al., "Tumour localisation kinetics of photofrin and three synthetic porphyrinoids in an amelanotic melanoma of the hamster," *Br. J. Cancer*, 68:225–234, 1993.

Lingam, et al., "Intraoperative Identification of sentinel lymph node in patients with malignant melanoma," *British Journal of Cancer*, 75(10), 1505–1508, May, 1997.

McCartney, A.C.E., "Pathology of ocular melanomas," *British Medical Bulletin*, 51:678–693, 1995.

Mellado, et al., "Detection of Circulating Neoplastic Cells by Reverse–Transcriptase Polymerase Chain Reaction in Malignant Melanoma: Association with Clinical Stage and Prognosis," *Journal of Clinical Oncology*, 14:2091–2097, 1996.

Menon, et al., "Inhibition of lung metastasis in mice induced by B16F10 melanoma cells by polyphenolic compounds," *Cancer Letters*, 95:221–225, 1995.

Morgan, et al., "Second Generation Sensitizers: Where Are We and Where Should We Be Going?" *Future Directions and Applications in Photodynamic Therapy*, pp. 87–106, SPIE Institute Series vol. IS 6, 1990.

Nannmark, et al., Microvessel Origin and Distribution in Pulmonary Metastases of B16 Melanoma: Implication for Adoptive Immunotherapy, *Cancer Research*, 55:4627–4632, 1995.

Nelson, et al., "Photodynamic Therapy of Human Malignant Melanoma Xenografts in Athymic Nude Mice," *Journal of the National Cancer Institute*, 80:56–60, 1988.

Pharmacyclics Press Release, "Pharmacyclics Completes Phase I Lu–Tex Trials in Photodynamic Cancer Treatment," Sunnyvale, California, Jan. 7, 1997.

Pharmacyclics Press Release, "Pharmacyclics Expands Photodynamic Therapy Trial to Stanford," Sunnyvale, California, Mar. 28, 1996.

Pharmacyclics Press Release, "Pharmacyclics Present Results and Updates Status for Photodynamic Therapy Agent at ASCO Meeting," Sunnyvale, California, May 19, 1997.

Pharmacyclics Press Release, "Pharmacyclics, Hoechst Celanese Forge Manufacturing Pact for Photodynamic Therapy and Radiation Sensitizer Products," Sunnyvale, California, Sep. 12, 1996.

Pharmacyclics Press Release, "Pharmacyclics' Photodynamic Therapy Agent Lu–Tex is Well Tolerated and Demonstrates Activity in a Multicenter Phase I Cancer Trial," Sunnyvale, California, Jun. 17, 1996.

Sealy, et al., "Photosensitization of Melanin: An Electron Spin Reasonance Study of Sensitized Radical Production and Oxygen Consumption," *Photochemistry and Photobiology*, 40:453–459, 1984.

Sessler, et al., "Anion binding: a new direction in porphyrin–related research," *Pure & Appl. Chem.*, 65(3):393–398, 1993.

Sessler, et al., "Expanded Porphyrins, Receptors for Cationic, Anionic, and Neutral Substrates," *Transition Metals in Supremolecular Chemistry*, L. Fabbrizzi and A. Poggi, Editors, NATO ASI Series, Kluwer, Amsterdam, pp. 391–408, 1994.

Sessler, et al., "Gadolinium (III) Texaphyrin: A Novel MRI Contrast Agent," *J. Am. Chem. Soc.*, 115:10368–10369, 1993.

Sessler, et al., "Preparation of Lanthanide (III) Texaphyrin Complexes and Their Applications to Magnetic Resonance Imaging and Photodynamic Therapy," *INOR (300) Abstracts of Papers Part 1, 204th ACS National Meeting 0–8412–2467–6, American Chemical Society, Washington, D.C.*, Aug. 23–28, 1992.

Sessler, et al., "Synthesis and Applications of Schiff–Base Derived 'Expanded Porphyrins'", *INOR (100) Abstracts of Papers Part 1, 204th ACS National Meeting 0–8412–2467–6, American Chemical Society, Washington, D.C., Aug. 23–28, 1992.*

Sessler, et al., "Synthesis and Binding Properties of Monomeric and Dimeric Guanine and Cytosine Amine Derivatives," *J. Org. Chem.*, 57:818–826, 1992.

Sessler, et al., "Synthesis and Structural Characterization of Lanthanide (III) Texaphyrins," *Inorganic Chemistry*, 32:3175–3187, 1993.

Sessler, et al., "Texaphyrins: Synthesis and Applications," *Acc. Chem. Res.*, 27(2):43–50, 1994.

Sessler, et al., "Tripyrroledimethine–derived ("texaphyrin–"–type) macrocycles: Potential photosensitizers which absorb in the far–red spectral region," *SPIE Proc. Soc. Opt. Eng.*, 1426:318–329, 1991.

Sessler, J.L. and A.K. Burrell, "Expanded Porphyrins," *Topics in Current Chemistry*, 161:180–273, 1991.

Sessler, J.L., "Texas–Sized Molecule," *Discovery*, 13(1):44–49, 1993.

Thaller, et al., "Potential use of Radiolabelled Porphyrins for Tumor Scanning," *Porphyrin Photosensitization*, Kessel and Dougherty, Eds., Plemun Press, New York and London, Publisher, pp. 265–278, 1983.

Thursfield, et al, Ed., "Skin cancer," *Canstat*, 20:2–15, Mar. 1995.

van Gemert, et al., "Is There An Optimal Laser Treatment for Port Wine Stains?" *Lasers in Surgery and Medicine*, 6:76–83, 1986.

Woodburn, et al., "Biological Analysis of Lutetium Texaphyrin," *Abstracts of the 24th Annual Meeting of the American Society for Photobiology*, p. 80S, Jun. 1996.

Young, et al., "Preclinical Evaluation of Gadolinium (III) Texapyrin Complex–A New Paramagnetic Contrast Agent for Magnetic Resonance Imaging," *Investigative Radiology*, 29(3):330–338, 1994.

International Search Report PCT/US 97/05332, mailed Jul. 21, 1997.

Stedman's Medical Dictionary: melaniferous, melanocyte, melanoderma, melanodermic, pp. 936–937, $25^{th}$ edition, 1990.

Dialog File Supplier: File 187:F–D–C Reports; The Pink Sheet, vol. 58, No. 27, "Pharmacyclics Gd–Tex for brain metastases in Phase I/II multicenter trial, " Jul. 1, 1996.

Dialog File Supplier File 187: F–D–C Reports; Pharmaceutical Approvals Monthly, vol. 1, No. 7, "Clinical Trial Updates: Company–Sponsored Studies: Pharmacyclics," Jul. 1, 1996.

Dialog File Supplier: File 129: PHIND AN=00414390, "Pharmacyclics' Gadolite to enter Phase III clinical trials," Aug. 30, 1994.

Search to Melanin and detection, May 8, 1997.

Search, 1996, prior to Mar. 26, 1996.

U.S. Serial No. 08/484,551 to Sessler et al. filed Jun. 7, 1995.

U.S. Serial No. 08/458,347 to Sessler et al. filed Jun. 2, 1995.

U.S. Serial No. 08/591,318 to Young et al. filed Jan. 25, 1996.

U.S. Serial No. 08/763,451 to Young et al. filed Dec. 11, 1996.

U.S. Serial No. 08/914,272 to Woodburn et al. filed Aug. 19, 1997.

International Search Report dated Dec. 1, 1998 for PCT/US98/15833.

Moretti, J.L., Labeled Iodoquines for the Scintigraphy of Melanin Tumors, *Chem. Abstr.*, 77(15):411, Col. 2; Oct. 1972.

USE OF TEXAPHYRINS IN DETECTION OF MELANIN AND MELANIN METABOLITES DIAGNOSTIC OF MELANOTIC MELANOMA

FIELD OF THE INVENTION

The present invention relates generally to the fields of cancer diagnosis, and particularly to methods for diagnosis of melanotic melanoma or metastatic melanotic melanoma. The use of texaphyrins for in vivo or in vitro detection of melanin or melanin metabolites diagnostic of melanotic melanoma is provided herein. A further aspect of the invention is a method of identifying, localizing, and diagnosing melanin-containing cells or tissues.

BACKGROUND OF THE INVENTION

The incidence and mortality rates of malignant melanoma continue to rise dramatically throughout the world. In the United States, it is estimated that one in 90 Americans will develop melanoma by the year 2000. Melanoma is one of the most feared neoplasms because of the high mortality associated with metastatic involvement.

Malignant melanoma is commonly found in early stages in the form of a skin lesion. The lesion often results from the transformation of a preexisting nevus or discolored patch of skin containing aggregates of melanocytes. The best prognostic factor for determining the presence of metastatic disease is the depth of invasion of the primary lesion. Lesions with a depth greater than 0.8 mm have an increased risk for metastases. Melanomas usually metastasize first via the lymphatic system, with involvement of regional nodes, and then via blood vessels, with dissemination to subcutaneous tissue and to the liver, lungs, and brain. The presence of regional lymph node metastasis is predictive of a poor prognosis.

Malignant melanomas arise from melanocytes and can be pigmented (melanotic) due to accumulation of melanin, which imparts a dark color to these lesions. Due to the fact that some melanocytes may be less well-differentiated and therefore produce little or no melanin, these malignant lesions may also be nonpigmented or amelanotic.

Melanins are pigments responsible for the dark color of skin, hair, feathers, fur, insect cuticle, the choroid coat of the eye, and the substantia nigra of the brain. Melanins are also found in plants, fungi, bacteria, and pathological human urine where they can be an indication of melanotic tumors. These pigments are synthesized into the skin by melanocytes; they have a broad absorption spectrum from 250 nm–1,200 nm and are sometimes referred to as providing a "light absorbing mantle." Eumelanins (sepiomelanin, melanoma-melanin) and phaeomelanins are found in the animal kingdom, the latter group being lighter in color. Allomelanins are most often present in bacteria and plants. The chemical units that predominate in these melanins are indole-related, formed from tyrosine and dopa precursors.

Production of melanin is termed melanogenesis and is strictly compartmentalized to melanosomes, highly specialized organelles of melanocytes. Through dendritic extensions of the melanocyte, melanins are transferred to keratinocytes, resulting in pigmentation of the skin.

Physicians currently use CT scans, radionuclide bone scans, liver and spleen scintigraphy, and magnetic resonance imaging to evaluate the extent of melanoma. Usually these tests are conducted when specific symptoms require investigation. However, these diagnostic modalities are not specific for melanoma; biopsy is currently the only recognized definitive means of identifying the cause of a lesion.

Melanoma tumor-associated antigens expressed by melanoma cells have been used as a target for radioimmunoscintigraphy with radiolabeled antibodies. Radiolabeled monoclonal antibodies having specificity for particular cell types can identify the cellular composition of intact lesions. However, antigens expressed on the surface of melanoma cells are only somewhat melanoma-specific. Nonspecific localization of antibody conjugates in liver, spleen, and bone marrow is a significant problem in image interpretation. In addition, micrometastatic lesions are not able to be localized.

Sentinel nodes, the lymph nodes nearest the site of the primary melanoma tumor on the direct lymph drainage pathway, are identified by injecting patent blue-V or isosulfan intradermally at the site of the primary melanoma. If tumor is found in the sentinel node, then a full lymphadenectomy is carried out. Lymphatic channels are visualized during dissection and traced to the sentinel lymph node. A regional lymph node basin can be identified by cutaneous lymphoscintigraphy with technetium-labeled dextran in patients whose melanoma has an ambiguous drainage route.

Early detection of melanoma is highly desirable for patient prognosis. Circulating melanoma cells can be detected by cytometric methods and by using reverse transcriptase-polymerase chain reaction to detect tyrosinase messenger ribonucleic acid which is correlated with circulating melanoma cells. Melanin metabolites can be detected by HPLC, histology, or by immunohistochemical techniques. ARUP Laboratories (Salt Lake City, Utah) appears to provide a colorimetric test for melanin in urine (www.aruplab.com/ug/ugar1399.htm, updated Apr. 1, 1997), although the reagent used is not specified.

A solution of sodium nitroferricyanide, also known as Thormahlin reagent, has been used by clinicians to detect urinary melanin for medical diagnostic purposes, such as for detection of melanoma. Melanin is detected by observance of a color change after the addition of sodium nitroferricyanide to an aliquot of urine. Depending upon the levels of melanin present in the sample, the mixture will change from a normal straw color to green, blue, brown, or black.

Demelanizing test samples of urine so that melanin does not interfere with testing for marijuana is reported by U.S. Pat. No. 4,843,020. Reagents such as sodium nitroferricyanide, acidified ferric chloride in water, hydroquinone (p-dihydroxybenzene), monobenzone (monobenzyl ether of hydroquinone), an ammoniacal silver nitrate solution in water, or certain mono- and dihydroxybenzene derivates such as catechol, 4-t-butyl-catechol, 3-methylcatechol, 3,4-dihydroxyphenylalanine, 3,4-dihydroxyphenylacetic acid, and 4-methoxyphenol are cited as capable of removing melanin from urine samples.

Certain metabolites of melanin serve as diagnostic markers or monitoring indices for melanoma. Jimbow et al. (*Society for Investigative Dermatology, Inc.* 100:No. 3, Supplement, March, 1993) have reported that the synthesis of pheomelanin is markedly increased in malignant melanoma and dysplastic nevi, that high levels of metabolites of pheomelanin and eumelanin can be detected in the blood and urine of patients with metastatic melanomas, that the release of melanin metabolites correlates with tumor thickness and tumor load including the extent of metastases, that synthesis of melanosomal proteins becomes aberrant in malignant melanoma, and that antigenic epitopes uniquely expressed in malignant melanoma can be identified.

Methylene blue, a phenothiazine derivative, is reported to have affinity for melanin and has been introduced to clinical trials for diagnosis and therapy.

U.S. Pat. No. 4,749,559 reportedly discloses a method of detecting melanin-containing matter by reacting melanin-containing matter with an enantiomer of 2,3,4,5-tetrahydro-3-methyl-5-phenyl-1H-3-benzazepin-7-ol (BZZ) and determining the binding of the enantiomer with melanin. The detecting requires that the enantiomer be labeled with a radioactive compound such as $^{125}$I. BZZ appears in the normal brain (caudate) at levels that may be toxic and appears significantly less tumor-specific than an ideal detecting agent.

U.S. Pat. No. 5,310,539 to Williams, incorporated herein by reference, reportedly provides melanin-based agents for image enhancement. Native or synthesized melanin is reported to act as a contrast agent by itself, however, incorporating a paramagnetic metal into the melanin polymer enhances significantly its ability to affect contrast in magnetic resonance imaging (MRI). Natural melanin is cited as possibly having some endogenous metals but such metals do not cause a relaxation effect similar to those provided by Williams. The high toxicity of gadolinium is cited as making it unlikely to be available for incorporation into a natural melanin produced in vivo. These melanin-based contrast agents, therefore, are not useful for detecting in vivo melanin, or melanin being assayed in an in vitro assay.

The challenge remains to develop low-cost, readily available, and highly sensitive, specific, laboratory tests to improve the diagnosis and monitoring of malignant melanotic melanoma. An ideal agent would also be capable of being stably labeled, and when used in vivo, would be nontoxic and quickly cleared from the system.

Texaphyrins are aromatic pentadentate macrocyclic "expanded porphyrins" useful as MRI contrast agents, as radiosensitizers, as chemosensitizers, and in photodynamic therapy. Texaphyrin is considered as being an aromatic benzannulene containing both 18p- and 22p-electron delocalization pathways. Texaphyrin molecules absorb strongly in the tissue-transparent 700–900 nm range, and they exhibit inherent selective uptake or biolocalization in certain tissues, particularly regions such as, for example, liver, atheroma or tumor tissue. Texaphyrins have exhibited significant tumor selectivity as detected by fluorescence and magnetic resonance imaging. Texaphyrins and water-soluble texaphyrins, method of preparation and various uses have been described in U.S. Pat. Nos. 4,935,498; 5,162,509; 5,252,720; 5,256,399; 5,272,142; 5,292,414; 5,369,101; 5,432,171; 5,439,570; 5,451,576; 5,457,183; 5,475,104 5,504,205; 5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; and 5,622,946; PCT publications WO 90/10633, 94/29316, 95/10307, 95/21845, 96/09315, 96/38461 and 96/40253; allowed U.S. patent applications Ser. Nos. 08/484,551, 08/591,318 and 08/624,311; and pending U.S. patent applications Ser. Nos. 08/458,347, 08/657,947, 08/700,277 and 08/763,451; each patent, publication, and application is incorporated herein by reference.

U.S. Food and Drug Administration phase I clinical trials of the texaphyrin photosensitizer, lutetium texaphyrin, for the photodynamic treatment of metastatic cancers involving the skin or subcutaneous tissue have been completed, and phase II testing is in progress. Gadolinium texaphyrin is currently in a multi-center phase Ib/II trial for the treatment of brain metastases.

The present invention overcomes cited problems with prior art methods of melanin and melanoma detection by providing texaphyrins or texaphyrin metal complexes as detection reagents for the presence of melanin and melanin metabolites that are predictive of the presence of melanotic melanoma.

SUMMARY OF THE INVENTION

The present invention results from a fluorescent microscopic demonstration that lutetium texaphyrin is highly concentrated in the melanosomes of melanotic melanoma cells and collects at the dendritic processes that pass melanin to keratinocytes of the skin. The affinity that texaphyrin has for melanin and melanosomes demonstrates that texaphyrin may be used for detection and assay for the presence of melanin and melanin metabolites as a diagnosis of melanotic melanoma or melanotic melanoma metastasis.

Accordingly, the present invention provides a method for determining presence of melanin or a melanin metabolite in a test subject comprising contacting a detectable texaphyrin with the test subject, and determining binding of the detectable texaphyrin with melanin or the melanin metabolite. Binding demonstrates presence of melanin or the melanin metabolite in the test subject. The test subject is preferably an animal or a human. The contacting may be by administration of a detectable texaphyrin to the animal or human, and determining binding is by imaging the human using imaging methods as described herein. A body sample such as urine, blood, plasma, or tissue, such as lymph node tissue, may be collected from a patient having been administered a texaphyrin or texaphyrin metal complex for in vitro analysis of the presence of texaphyrin. In this case, binding is determined by in vitro assay methods using fluorescent spectroscopy, optical coherence tomography (OCT), or back-scattered infrared light, for example.

Alternatively, the contacting may be by adding a detectable texaphyrin to a body sample from a patient to be tested and not having been administered a texaphyrin, and determining the presence of the detectable texaphyrin in an in vitro assay of the body sample. The body sample may be tissue, such as lymph node tissue, blood, plasma, serum, urine, or any other body tissue capable of being tested for presence of melanin or a melanin metabolite.

In general, texaphyrin would be administered to a subject for detection of systemic malignancies involving whole tissues. Texaphyrin would be added to an in vitro sample to assay tumor burden in blood or urine.

When the detectable texaphyrin is fluorescent, determining binding of the detectable texaphyrin is by observing fluorescence of the texaphyrin. When the detectable texaphyrin is complexed with a paramagnetic metal cation, determining binding of the detectable texaphyrin is by fluorescence or by magnetic resonance imaging. Further methods for determining binding include x-ray imaging, Raman scattering, magnetometry (bioluminescence), OCT, reflectance, gamma scanning when the texaphyrin is complexed with a gamma-emitting isotope, or α-, or β-emission detection when the texaphyrin is complexed with or bound to an α-, or a β-emitting isotope. For fluorescent detection, texaphyrins may be activated by 400–500 nm light (the Soret band) or 700–900 nm light, preferably 700–800 nm, (the Q band) and, therefore, provide considerable versatility for use in humans.

In another embodiment of the present invention, a method is provided for determining abnormal presence of melanin or a melanin metabolite in a test subject compared to a control subject. The method comprises contacting a detectable texaphyrin with the test subject, and with the control subject; and determining binding of the detectable texaphyrin with melanin or the melanin metabolite in the test subject, and in the control subject; wherein when binding of the texaphyrin in the test subject is greater than binding of texaphyrin in the control subject, an abnormal presence of melanin or a melanin metabolite is present in the test subject.

A test kit for determining abnormal presence of melanin or a melanin metabolite in a biological sample is a further embodiment of the present invention. The kit comprises in packaged combination a carrier means adapted to receive a plurality of container means in close confinement therewith, a first container means including a detectable texaphyrin, a second container means including a control sample, and a mechanism for determining the binding of the detectable texaphyrin to melanin or to a melanin metabolite.

A further embodiment of the present invention is a method for diagnosing melanotic melanoma in a patient comprising administering a detectable texaphyrin to the patient; obtaining a urine, blood, plasma, or tissue test sample from the patient; and determining binding of the detectable texaphyrin with melanin or the melanin metabolite in the test sample, wherein when binding of the texaphyrin in the test sample is greater than binding of texaphyrin in a control sample, melanotic melanoma is diagnosed in the patient.

A further method for diagnosing melanotic melanoma in a patient comprises obtaining a urine, blood, plasma, or tissue test sample from the patient; contacting the test sample and a control sample with a detectable texaphyrin; and determining binding of the detectable texaphyrin with melanin or the melanin metabolite in the test sample and in the control sample, wherein when binding of the texaphyrin in the test sample is greater than binding of texaphyrin in the control sample, melanotic melanoma is diagnosed in the patient.

A method for diagnosis of metastasis of melanotic melanoma in a patient is a further aspect of the present invention. The method comprises administering a detectable texaphyrin intradermally to the patient near a site of primary melanoma, allowing the texaphyrin to pass to a lymph basin; and following a lymphatic channel from the site of primary melanoma to a lymph node by detecting presence of the texaphyrin, wherein presence of texaphyrin in the lymph node is diagnostic of metastasis of melanoma in the patient. Preferably, detecting is by fluorescence, or by lymphoscintigraphy.

Texaphyrins having aqueous solubility provide an advantage in the methods of the present invention, providing for rapid infusion as a bolus as compared to benzoporphyrin derivative and tetra(m-hydroxyphenyl)chlorin which require lipid environments; and further obviating the need for a lipophilic carrier, use of liposomes, or use of a pump. Texaphyrins can be administered in a bolus injection allowing for a sufficiently large amount of drug to be present in the blood and for fast-turnaround between dosing and treatment. Further, texaphyrins are cleared quickly from the body; no toxicity has been observed in the use of texaphyrins in the present invention. Texaphyrins can be administered in multiple doses; for example, in related trials, Phase II patients have received ten injections over a 2-week period.

Following long-standing patent law convention, the terms "a" and "an" mean "one or more" when used in this application, including the claims.

DETAILED DESCRIPTION OF THE PREFERRED EMBODIMENTS

Melanotic melanoma tumor or cells, melanin, or melanin metabolites are detected, identified, and localized when bound to texaphyrins or texaphyrin metal complexes. Therefore, the present invention provides texaphyrins and texaphyrin metal complexes as reagents for in vivo or in vitro detection for melanin or melanin metabolites predictive of the presence of melanotic melanoma and metastasis of melanotic melanoma.

"melanotic melanoma" is meant a malignant neoplasm derived from cells that form melanin.

By "melanin" is meant a dark brown to black polymer pigment of indole 5,6-quinone and/or 5,6-dihydroxyindole 2-carboxylic acid that occurs in the skin, hair, or pigmented coat of the retina, for example. The term "melanin" includes eumelanin, pheomelanin, or allomelanin. Melanin is negatively charged and contains relatively stable free radicals, i.e., unpaired electrons, and appears to be somewhat paramagnetic when found in melanoma. While not wanting to be bound by theory, the present inventors believe that texaphyrin and texaphyrin metal complexes (which have a positively charged macrocyclic ring) have affinity for melanin due to the attraction between the positively charged texaphyrin and the negatively charged melanin. Melanin is stored in melanosomes, and melanosomes can comprise up to 40% of the dry weight of melanoma.

By "melanin metabolite" is meant a substance taking part in or produced by metabolic activity related to melanin. "Melanin metabolite" includes melanin precursor molecules, dopa precursor molecules, and melanin breakdown products. Exemplary melanin metabolites include, but are not limited to, molecules such as dihydroxyphenylalanine, a dihydroxyphenylalanine derivative, 5-S-cysteinyldopa, a methylated 5,6-dihydroxyindole, a methylated 5,6-dihydroxyindole-2-carboxylic acid, 6-hydroxy-5-methoxyindole-2-carboxylic acid, or 5-hydroxy-6-methoxyindole-2-carboxylic acid.

Several clinical types of melanoma have been recognized. Those containing melanin or melanin metabolites are expected to be detectable by using texaphyrins and include the following: acral lentiginous, benign juvenile, Cloudman, halo, Harding-Passey, malignant, malignant in situ, melanotic lentigo (Hutchinson freckle), minimal deviation, nodular, subungual, superficial spreading, desmoplastic, retinal or ocular melanoma, and neurotropic melanoma, for example.

Examples of texaphyrins or texaphyrin metal complexes for use in detection of melanin or melanin metabolites are those having structure I or II:

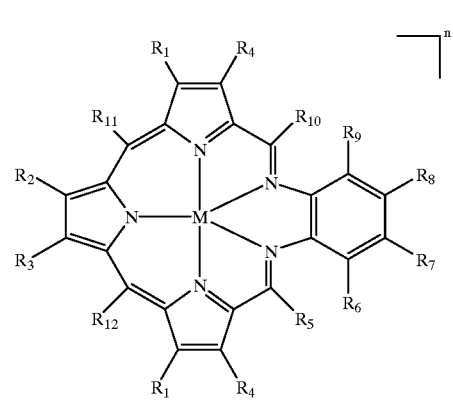

-continued

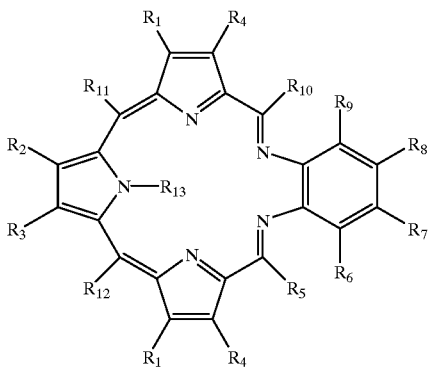

II

M is H, a divalent metal cation, or a trivalent metal cation. Preferably, M is a divalent metal cation, or a trivalent metal cation. A preferred divalent metal cation is Ca(II), Mn(II), Co(II), Ni(II), Zn(II), Cd(II), Hg(II), Fe(II), Sm(II), Cu(II) or $UO_2$(II). A preferred trivalent metal cation is Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), Ga(III), or U(III). Most preferred trivalent metal cations are Lu(III) and Gd(III).

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, or aminoalkyl.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, or aminoalkyl; and n is an integer value less than or equal to 5.

$R_{13}$ is alkyl, alkenyl, oxyalkyl, or hydroxyalkyl having up to about 3 carbon atoms and having rotational flexibility around a first-bound carbon atom. Rotational flexibility allows the rest of the group to be positioned outside the plane of the texaphyrin. Thus, for example, a preferred alkenyl is $CH_2$—$CH$=$CH_2$. The pyrrole nitrogen substituent is most preferably a methyl group. A texaphyrin having a methyl group attached to a ring nitrogen is described in U.S. Pat. No. 5,457,183, incorporated by reference herein.

Fluorescent texaphyrins may be used for detection of melanin or melanin metabolites. The term "fluorescent", as used herein, means that upon excitation by light associated with the absorption profile of texaphyrin, light is emitted at a longer wavelength by the irradiated texaphyrin. All texaphyrins are fluorescent, albeit, to varying degrees, and texaphyrins complexed with Y(III), Lu(III), Gd(III), Dy(III), Eu(III), or Mn(III) are particularly preferred as fluorescent texaphyrins, for example.

In addition to fluorescent detection, texaphyrins or texaphyrin metal complexes may be imaged by x-radiation, Raman scattering, optical coherence tomography, infrared detection, planar and single photon emission computed tomography (SPECT) γ-detection, or α-, or β-detection for radiolabelled molecules, or by magnetometry; further, texaphyrins complexed with a paramagnetic metal cation may be used for magnetic resonance imaging. Preferred paramagnetic metal cations include Mn(II), Mn(III), Fe(III), or trivalent lanthanide metals other than La(III), Lu(III), and Pm(III). More preferably, the paramagnetic metal is Mn(II), Mn(III), Dy(III), or Gd(III); most preferably, Gd(III). Any of various types of magnetic resonance imaging can be employed in the practice of the invention, including, for example, nuclear magnetic resonance (NMR), NMR spectroscopy, electronic spin resonance (ESR), and magnetic spin resonance (MRS). The preferred imaging technique is NMR.

Gamma particle detection may be used to image a texaphyrin complexed to a gamma-emitting metal. [51]Chromium, [68]gallium, or [111]indium are preferred metals for complexing to texaphyrins for gamma particle scanning. Imaging of a texaphyrin complexed to an α-emitter or to a β-emitter such as described in U.S. Pat. Nos. 4,935,498 or 5,252,720, previously incorporated by reference herein, is by detection of α- or β- emission, respectively. Monochromatic X-ray photon sources may be used for imaging also.

In the above-described structure I, "n" will typically be an integer value less than or equal to 5. In the context of the basic macrocycle with a divalent or trivalent metal cation, n is 1 or 2; however, one skilled in the art in light of the present disclosure would realize that the value of n would be altered due to charges present on substituents $R_1$–$R_{12}$ and charges present on the covalently bound site-directing molecule. It is understood by those skilled in the art that the complexes described in the present invention have one or more additional ligands providing charge neutralization and/or coordinative saturation to the metal ion. Such ligands include chloride, nitrate, acetate, and hydroxide, among others.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonene and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, and the term as used herein includes both unsubstituted aryls and aryls substituted with one or more nitro, carboxy, sulfonic acid, hydroxy, oxyalkyl or halide substituents. In this case, the substituent on the phenyl or naphthyl may be added in a synthetic step after the condensation step which forms the macrocycle.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$ alkyls being preferred, and diols of $C_{1-3}$ alkyls being more preferred; and polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. "Oxyalkyl" is meant to include polyethers with one or more functional groups. The number of repeating oxyalkyls within a substituent may be up to 200, preferably is from 1–20, and more preferably, is 1–10, and most preferably is 1–5. A preferred oxyalkyl is $O(CH_2CH_2O)_xCH_3$ where x=1–100, preferably 1–10, and more preferably, 1–5.

"Oxyhydroxyalkyl" means alkyl groups having ether or ester linkages, hydroxyl groups, substituted hydroxyl groups, carboxyl groups, substituted carboxyl groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5)_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R'' is a functional group as described herein.

Representative examples of useful amines include a primary, secondary or tertiary amine of an alkyl as described hereinabove.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether or the like.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol.

In most preferred embodiments, appended groups are covalently bonded to the texaphyrin via a carbon-carbon, carbon-nitrogen, carbon-sulfur, or a carbon-oxygen bond, more preferably a carbon-oxygen or a carbon-nitrogen bond.

In the practice of the present invention, preferred functionalizations for texaphyrin I or II are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$ and $R_{12}$ are independently hydrogen, phenyl, lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl. The phenyl may be substituted or unsubstituted. In a presently preferred texaphyrin I or II, $R_1$ is $(CH_2)_2CH_2OH$, $R_2$ and $R_3$ are $CH_2CH_3$, $R_4$ is $CH_3$, $R_7$ and $R_8$ are $O(CH_2CH_2O)_2CH_2CH_2OCH_3$, $R_5$, $R_6$, and $R_9$–$R_{12}$ are H, and M is Lu(III) or Gd(III). These texaphyrins are named herein as LuT2BET or GdT2BET, respectively, (compound III where M=Lu(III), or M=(Gd(III)).

In other presently preferred texaphyrin compounds I or II, $R_1$–$R_{12}$ are as in Tables A and B for texaphyrins A1–A89, and M is as defined hereinabove. However, while the above-described texaphyrins are presently preferred compounds for use in the present invention, the invention is not limited thereto and any detectable texaphyrin may be useful for detection of melanin or melanin metabolites.

III
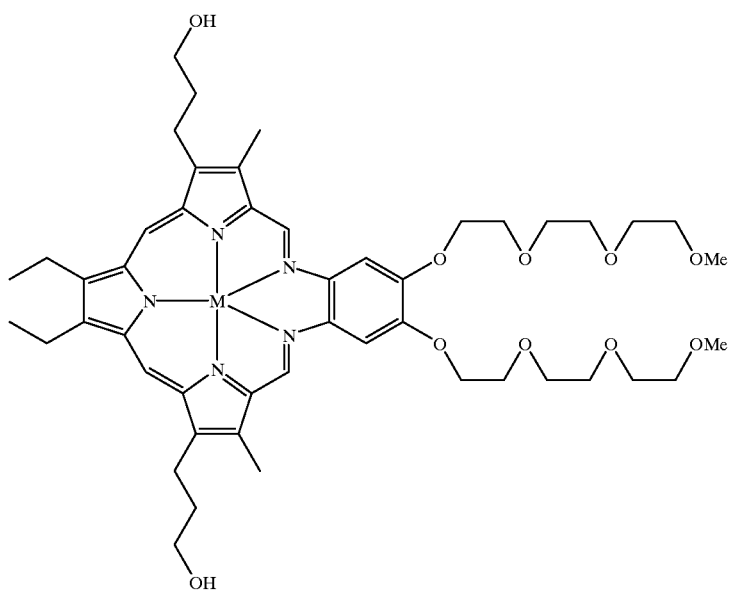

TABLE A

Representative Substituents for Texaphyrin Macrocycles A1–A89 of the Present Invention. Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | H |
| A2 | " | " | " | " | " | " |
| A3 | " | " | " | " | " | " |
| A4 | " | " | " | " | " | " |
| A5 | " | " | " | " | " | " |
| A6 | " | " | " | " | " | " |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | COOH | COOH | " | " | " |
| A13 | —$CH_2(CH_2)_2OH$ | $COOCH_2CH_3$ | $COOCH_2CH_3$ | $CH_3$ | H | H |
| A14 | $CH_2CH_2CON(CH_2CH_2OH)_2$ | $CH_2CH_3$ | $CH_2CH_3$ | " | " | " |
| A15 | $CH_2CH_2CON(CH_3)CH_2$-$(CHOH)_4CH_2OH$ | " | " | " | " | " |
| A16 | $CH_2CH_3$ | " | " | " | " | " |
| A17 | $CH_2(CH_2)_2OH$ | " | " | " | " | " |
| A18 | " | " | " | " | " | " |
| A19 | " | " | " | " | " | " |
| A20 | $CH_2CH_3$ | $CH_3$ | $CH_2CH_2COOH$ | " | " | " |
| A21 | " | " | $CH_2CH_2CONH$-$CH(CH_2OH)_2$ | " | " | " |
| A22 | $CH_2(CH_2)_2OH$ | $CH_2CH_3$ | $CH_2CH_3$ | " | " | " |
| A23 | " | " | " | " | " | " |
| A24 | " | " | " | " | " | " |
| A25 | " | " | " | " | " | " |
| A26 | " | " | " | " | " | " |
| A27 | " | COOH | COOH | " | " | " |
| A28 | " | $COOCH_2CH_3$ | $COOCH_2CH_3$ | " | " | " |
| A29 | $CH_2CH_2CONHCH(CH_2OH)_2$ | $CH_2CH_3$ | $CH_2CH_3$ | $CH_3$ | H | H |
| A30 | $CH_2CH_2ONHCH(CH_2OH)_2$ | " | " | " | " | " |
| A31 | $CH_2(CH_2)_2OH$ | " | $CH_2CH_2CONH$-$CH(CH_2OH)_2$ | " | " | " |
| A32 | " | " | $CH_2CH_2CONH$-$CH(CH_2OH)_2$ | " | " | " |
| A33 | $CH_2CH_3$ | $CH_3$ | $CH_2CH_2COOH$ | " | " | " |
| A34 | " | " | $CH_2CH_2CONH$-$CH(CH_2OH)_2$ | " | " | " |
| A35 | $CH_2CH_3$ | $CH_2CH_3$ | $CH_2CH_3$ | " | " | " |
| A36 | " | " | " | " | " | " |
| A37 | " | " | " | " | " | " |
| A38 | " | " | " | " | " | " |
| A39 | $CH_2(CH_2)_2OH$ | $CH_2CH_3$ | $CH_2CH_3$ | $CH_3$ | H | COOH |
| A40 | " | " | " | " | " | COOH |
| A41 | " | " | " | " | " | CONHCH-$(CH_2OH)_2$ |
| A42 | " | " | " | " | " | CONHCH-$(CH_2OH)_2$ |
| A43 | " | " | " | " | " | H |
| A44 | " | " | " | " | " | $OCH_3$ |
| A45 | " | " | " | " | " | " |
| A46 | " | " | " | " | " | " |
| A47 | " | " | " | " | " | " |
| A48 | " | " | " | " | " | " |
| A49 | " | " | " | " | " | " |
| A50 | " | " | " | " | " | $CH_3$ |
| A51 | " | " | " | " | " | " |
| A52 | " | " | " | " | " | " |
| A53 | " | " | " | " | " | " |
| A54 | " | " | " | " | $CH_3$ | H |
| A55 | " | " | " | " | " | " |
| A56 | " | " | " | " | " | " |
| A57 | $CH_2(CH_2)_2OH$ | $CH_2CH_3$ | $CH_2CH_3$ | $CH_3$ | $CH_3$ | H |
| A58 | " | " | " | " | " | " |
| A59 | " | " | " | " | " | " |
| A60 | " | " | " | " | " | " |
| A61 | " | " | " | " | " | " |
| A62 | " | " | " | " | " | " |
| A63 | " | " | " | " | " | OH |
| A64 | " | " | " | " | " | F |
| A65 | " | " | " | " | $CH_2(CH_2)_6OH$ | H |
| A66 | " | " | " | " | H | Br |
| A67 | " | " | " | " | " | $NO_2$ |

TABLE A-continued

Representative Substituents for Texaphyrin Macrocycles A1–A89 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A68 | " | " | " | " | " | COOH |
| A69 | " | " | " | " | " | $CH_3$ |
| A70 | " | " | " | " | $C_6H_5$ | H |
| A71 | " | COOH | COOH | " | $CH_2CH_3$ | " |
| A72 | " | $COOCH_2CH_3$ | $COOCH_2CH_3$ | " | $CH_3$ | " |
| A73 | $CH_2CH_2CON(CH_2CH_2OH)_2$ | $CH_2CH_3$ | $CH_2CH_3$ | " | " | " |
| A74 | $CH_2CH_2ON(CH_3)CH_2$ $(CHOH)_4CH_2OH$ | " | " | " | " | " |
| A75 | $CH_2CH_3$ | " | " | " | $CH_2(CH_2)_6OH$ | " |
| A76 | $CH_2(CH_2)_2OH$ | $CH_2CH_3$ | $CH_2CH_3$ | $CH_3$ | $CH_3$ or $CH_2CH_3$ | H |
| A77 | " | " | " | " | " | " |
| A78 | " | " | " | " | " | " |
| A79 | " | " | " | " | " | " |
| A80 | " | " | " | " | " | " |
| A81 | " | " | " | " | " | " |
| A82 | " | " | " | " | " | " |
| A83 | " | " | " | " | " | " |
| A84 | " | " | " | " | " | " |
| A85 | " | " | " | " | H | " |
| A86 | " | " | " | " | " | " |
| A87 | " | " | " | " | $CH_3$ or $CH_2CH_3$ | " |
| A88 | " | " | " | " | " | " |
| A89 | $CH_2CH_3$ | $CH_2CH_3$ | $CH_2CH_3$ | $CH_3$ | H | H |

TABLE B

Representative Substituents for Texaphyrin Macrocycles A1–A89 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A1 | $O(CH_2)_3OH$ | $O(CH_2)_3OH$ | H | H | H | H |
| A2 | $O(CH_2CH_2O)_3CH_3$ | $O(CH_2CH_2O)_3CH_3$ | " | " | " | " |
| A3 | $O(CH_2)_nCON(CH_2CH_2OH)_2$, n = 1–10 | " | " | " | " | " |
| A4 | $O(CH_2)_nCON(CH_2CH_2OH)_2$, n = 1–10 | H | " | " | " | " |
| A5 | $OCH_2CONC(CH_2OH)_3$ | " | " | " | " | " |
| A6 | $O(CH_2CH_2O)_3CH_3$ | " | " | " | " | " |
| A7 | $OCH_2CON(CH_2CH_2OH)_2$ | $O(CH_2CH_2O)_3CH_3$ | " | " | " | " |
| A8 | $OCH_2CONC(CH_2OH)_3$ | " | " | " | " | " |
| A9 | $O(CH_2CH_2O)_{100}CH_3$ | " | " | " | " | " |
| A10 | $OCH_2CON(CH_2CH_2OH)_2$ | H | " | " | " | " |
| A11 | $CH_2CON(CH_3)CH_2$-$(CHOH)_4CH_2OH$ | " | " | " | " | " |
| A12 | $CH_2CON(CH_3)CH_2$-$(CHOH)_4CH_2OH$ | " | " | " | " | " |
| A13 | $CH_2CON(CH_3)CH_2$-$(CHOH)_4CH_2OH$ | H | H | H | H | H |
| A14 | $CH_2CON(CH_3)CH_2$-$(CHOH)_4CH_2OH$ | " | " | " | " | " |
| A15 | $OCH_3$ | $OCH_3$ | " | " | " | " |
| A16 | $OCH_2CO_2CH_2C(CH_2OH)_3$ | H | " | " | " | " |
| A17 | $O(CH_2)_nCOOH$, n = 1–10 | | " | " | " | " |
| A18 | $(CH_2)_n$—$CON(CH_2CH_2OH)_2$, n = 1–10 | " | " | " | " | " |
| A19 | $YCOCH_2C(CH_2OH)_3$, Y = NH,O | " | " | " | " | " |
| A20 | $O(CH_2)_2CH_2OH$ | $O(CH_2)_2CH_2OH$ | " | " | " | " |
| A21 | " | " | " | " | " | " |
| A22 | $OCH_2COOH$ | $O(CH_2CH_2O)_3CH_3$ | " | " | " | " |
| A23 | $O(CH_2)_nCONC(CH_2OH)_3$, n = 1–10 | H | " | " | " | " |
| A24 | $O(CH_2CH_2O)_3CH_3$ | $O(CH_2CH_2O)_nCH_2C$-$(CH_2OH)_3$, n = 1–10 | " | " | " | " |
| A25 | $OCH_3$ | $OCH_2CONC(CH_2OH)_3$ | " | " | " | " |
| A26 | " | $CH_2CONC(CH_2OH)_3$ | " | " | " | " |
| A27 | " | " | " | " | " | " |
| A28 | $OCH_3$ | $CH_2CONC(CH_2OH)_3$ | H | H | H | H |
| A29 | " | $OCH_3$ | " | " | " | " |
| A30 | " | " | " | " | " | " |
| A31 | H | $O(CH_2)_nCOOH$, n = 1–10 | " | " | " | " |
| A32 | " | $(CH_2)_n$—$CON(CH_2CH_2OH)_2$, | " | " | " | " |

TABLE B-continued

Representative Substituents for Texaphyrin Macrocycles A1–A89 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A33 | $OCH_3$ | $O(CH_2CH_2O)_3$—$CH_3$, n = 1–10 | " | " | " | " |
| A34 | " | " | " | " | " | " |
| A35 | H | $O(CH_2)_nCONC(CH_2OH)_3$, n = 1–10 | " | " | " | " |
| A36 | $OCH_3$ | $O(CH_2)_nCONH(CH_2OH)_3$, n = 1–10 | " | " | " | " |
| A37 | $O(CH_2CH_2O)_3CH_3$ | $O(CH_2)_nCONH(CH_2OH)_3$, n = 1–10 | " | " | " | " |
| A38 | " | $O(CH_2CH_2O)_nCH_2C$-$(CH_2OH)_3$, n = 1–10 | " | " | " | " |
| A39 | $O(CH_2)_3OH$ | $O(CH_2)_3OH$ | $O(CH_2)_3OH$ | H | H | H |
| A40 | $O(CH_2CH_2O)_3CH_3$ | $O(CH_2CH_2O)_3CH_3$ | COOH | " | " | " |
| A41 | $O(CH_2CH_2O)_3CH_3$ | $O(CH_2CH_2O)_3CH_3$ | $(CH_2)_3OH$ | " | " | " |
| A42 | " | " | $O(CH_2CH_2O)_3CH_3$ | " | " | " |
| A43 | " | $O(CH_2)_3COOH$ | $O(CH_2CH_2O)_3CH_3$ | " | " | " |
| A44 | H | $OCH_2COOH$ | $OCH_3$ | " | " | " |
| A45 | " | $OCH_2COOH$ | " | " | " | " |
| A46 | " | $O(CH_2CH_2O)_3CH_3$ | " | " | " | " |
| A47 | $O(CH_2CH_2O)_3CH_3$ | " | " | " | " | " |
| A48 | " | $OCH_2CONC(CH_2OH)_3$ | " | " | " | " |
| A49 | " | $OCH_2COOH$ | " | " | " | " |
| A50 | " | $O(CH_2CH_2O)_3CH_3$ | $O(CH_2CH_2O)_3CH_3$ | " | " | " |
| A51 | " | $OCH_2COOH$ | $O(CH_2CH_2O)_3CH_3$ | " | " | " |
| A52 | $O(CH_2CH_2O)_3CH_3$ | $O(CH_2CH_2O)_{100}CH_3$ | $OCH_3$ | " | " | " |
| A53 | H | $OCH_2CONC(CH_2OH)_3$ | " | " | " | " |
| A54 | $O(CH_2)_3OH$ | $O(CH_2)_3OH$ | H | $CH_3$ | " | " |
| A55 | H | $O(CH_2CH_2O)_3CH_3$ | " | " | " | " |
| A56 | $O(CH_2CH_2O)_3CH_3$ | " | " | " | " | " |
| A57 | H | $OCH_2CONC(CH_2OH)_3$ | H | $CH_3$ | " | " |
| A58 | " | $OCH_2CONC(CH_2OH)_3$ | " | " | " | " |
| A59 | " | $OCH_2CON(CH_2CH_2OH)_2$ | " | " | " | " |
| A60 | $O(CH_2CH_2O)_3CH_3$ | $O(CH_2CH_2O)_{100}CH_3$ | " | " | " | " |
| A61 | " | $OCH_2CONC(CH_2OH)_3$ | " | " | " | " |
| A62 | H | $CH_2CON(CH_3)CH_2(CHOH)_4CH_2OH$ | " | " | " | " |
| A63 | $O(CH_2CH_2O)_3CH_3$ | $O(CH_2CH_2O)_3CH_3$ | OH | " | " | " |
| A64 | " | " | F | " | " | " |
| A65 | " | " | H | $CH_2(CH_2)_6OH$ | " | " |
| A66 | " | " | Br | H | " | " |
| A67 | " | " | $NO_2$ | " | " | " |
| A68 | " | " | COOH | " | " | " |
| A69 | " | " | $CH_3$ | " | " | " |
| A70 | " | " | H | $C_6H_5$ | " | " |
| A71 | " | " | " | $CH_2CH_3$ | " | " |
| A72 | " | " | " | $CH_3$ | " | " |
| A73 | " | " | " | " | " | " |
| A74 | $OCH_3$ | $OCH_3$ | " | " | " | " |
| A75 | H | $OCH_2CONC(CH_2OH)_3$ | " | $CH_2(CH_2)_6OH$ | " | " |
| A76 | $O(CH_2)_3OH$ | $O(CH_2)_3OH$ | H | $CH_3$ or $CH_2CH_3$ | $CH_3$ or $CH_2CH_3$ | $CH_3$ or $CH_2CH_3$ |
| A77 | $O(CH_2CH_2O)_3CH_3$ | $O(CH_2CH_2O)_3CH_3$ | " | " | $CH_3$ or $CH_2CH_3$ | $CH_3$ or $CH_2CH_3$ |
| A78 | $O(CH_2)_3OH$ | $O(CH_2CH_2O)_3CH_3$ | " | " | $CH_3$ or $CH_2CH_3$ | $CH_3$ or $CH_2CH_3$ |
| A79 | H | $O(CH_2)_nCONC(CH_2OH)_3$, n = 1,2,3 | " | " | $CH_3$ or $CH_2CH_3$ | $CH_3$ or $CH_2CH_3$ |
| A80 | H | $O(CH_2)_nCONC(CH_2OH)_3$, n = 1,2,3 | " | " | $CH_3$ or $CH_2CH_3$ | $CH_3$ or $CH_2CH_3$ |
| A81 | H | $O(CH_2)_3OH$ | " | " | $CH_3$ or $CH_2CH_3$ | $CH_3$ or $CH_2CH_3$ |
| A82 | $O(CH_2)_3OH$ | $O(CH_2)_nCONC(CH_2OH)_3$, n = 1,2,3, | " | " | $CH_3$ or $CH_2CH_3$ | $CH_3$ or $CH_2CH_3$ |
| A83 | $O(CH_2CH_2O)_3CH_3$ | $O(CH_2)_nCONC(CH_2OH)_3$, n = 1–10 | " | " | $CH_3$ or $CH_2CH_3$ | $CH_3$ or $CH_2CH_3$ |
| A84 | " | $O(CH_2)_nCONC(CH_2OH)_3$, n = 1,2,3 | " | " | $CH_3$ or $CH_2CH_3$ | $CH_3$ or $CH_2CH_3$ |
| A85 | " | $O(CH_2CH_2O)_3CH_3$ | " | " | $CH_3$ or $CH_2CH_3$ | $CH_3$ or $CH_2CH_3$ |

TABLE B-continued

Representative Substituents for Texaphyrin Macrocycles A1–A89 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A86 | " | " | " | " | $CH_2(CH_2)_2$ OH | $CH_2(CH_2)_2$ OH |
| A87 | " | " | " | $CH_3$ or $CH_2CH_3$ | $CH_2(CH_2)_2$ OH | $CH_2(CH_2)_2$ OH |
| A88 | " | $O(CH_2CH_2O)_3CH_3$ | " | " | $CH_2(CH_2)_2$ OH | $CH_2(CH_2)_2$ OH |
| A89 | $OCH_2CH_2CH_2OH$ | $OCH_2CH_2CH_2OH$ | H | H | H | H |

Importantly, texaphyrins may be synthesized using certain substituents to effect a lipid-water distribution coefficient that is optimal for use in detection of melanin and melanin metabolites, i.e., sufficiently water soluble for uptake into tissues and for ease of handling. "Water soluble" means soluble in aqueous fluids to about 1 mM or better. U.S. Patents, PCT publications, and pending applications to texaphyrins, methods of making and uses thereof have been listed herein and incorporated by reference herein. Sapphyrin compounds are disclosed in U.S. Pat. Nos. 5,041,078; 5,159,065; 5,120,411; 5,302,714; and 5,457,195; each patent is incorporated by reference herein.

One skilled in the art of organic synthesis in light of the present disclosure and the disclosures in the patents, applications and publications incorporated by reference herein could extend and refine the referenced basic synthetic chemistry to produce texaphyrins having various substituents.

For in vivo administration, texaphyrins are provided as pharmaceutical preparations. A pharmaceutical preparation of a texaphyrin may be administered alone or in combination with pharmaceutically acceptable carriers, in either single or multiple doses. Suitable pharmaceutical carriers include inert solid diluents or fillers, sterile aqueous solutions, and various organic solvents. The pharmaceutical compositions formed by combining a texaphyrin of the present invention and the pharmaceutically acceptable carriers are then easily administered in a variety of dosage forms. Administration may be intravenous, intraperitoneal, parenteral, intramuscular, subcutaneous, oral, or topical, with intravenous or topical administration being preferred, and intravenous being more preferred.

Solutions of the texaphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. Topical creams, emulsions, solutions, and the like are contemplated for applications to surface areas of the body. Topical application may also be by iontophoresis.

Pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The texaphyrin to be used in the detection methods of the invention will be administered in a pharmaceutically effective amount. By "pharmaceutically effective" is meant a dose that will provide an image for detection by any one of the imaging methods described herein. The specific dose will vary depending on the particular texaphyrin chosen, the dosing regimen to be followed, timing of administration, the tissue to be imaged, and the physical delivery system in which it is carried. A sufficient amount of texaphyrin is administered to produce an observable fluorescent emission when excited by light, preferably light having a wavelength in the range of about 400–500 nm, more preferably, about 430–500 nm and, most preferably, about 488 nm. Alternatively, texaphyrins may be excited by 700–900 nm light, preferably 700–800 nm light. Images are recorded by illuminating with light in the excitation wavelength range and detecting the amount of fluorescent light emitted at the emission wavelength of about 710–790 nm, preferably about 730–760 nm, and more preferably, at about 750 nm. Such dose can be determined without undue experimentation by methods known in the art or as described herein.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Fluorescent Microscopy of Texaphyrin in Melanoma Cells

The present example provides results from fluorescent microscopy studies using lutetium texaphyrin (LuT2BET) incorporated into melanoma cells.

B16F10 melanotic melanoma murine cells as described in Example 2 were incubated with 20 µg/ml LuT2BET for 1 to 24 h in Waymouth's medium supplemented with 15% fetal bovine serum. The adherent cells were washed thoroughly with PBS (3×) and examined using confocal laser scanning microscopy.

Lutetium texaphyrin was demonstrated to be highly concentrated in the melanosomes of melanoma cells and was demonstrated to collect at the dendritic processes that pass melanin to the keratinocytes of the skin.

These studies confirm that LuT2BET is capable of serving as a detection reagent for melanin and melanosomes.

EXAMPLE 2

Biodistribution of LuT2BET in Melanoma-Bearing Mice

The present example provides results from a study of the biodistribution of lutetium texaphyrin in melanoma-bearing mice. The biodistribution of LuT2BET was analyzed in C57 mice bearing B16 melanoma at 3 h, 5 h, and 24 h after an intravenous administration of 10 or 20 µmol/kg.

LuT2BET: The synthesis and chemical analysis of lutetium texaphyrin (LuT2BET, texaphyrin A2 of Tables A and B where M is lutetium) was provided in, for example, U.S. Pat. No. 5,622,946 and in PCT publication W095/10307. LuT2BET was dissolved in 5% mannitol at a 2 mM concentration. LuT2BET absorbs strongly in the far-red region of the electromagnetic spectrum, having a molar extinction coefficient of 23,000 $M^{-1}cm^{-1}$ in this solution at 732 nm.

Melanoma Cells: B16F10 melanotic melanoma murine cells were obtained from the University of California, San Francisco Cell Culture Facility. These cells are highly pigmented and metastatic in vivo. Cells were grown in Iscove's Modified Dulbeccos' Medium (Gibco, Grand Island, N.Y.) supplemented with 10% fetal bovine serum (JRH Biosciences, Woodland, Calif.) and penicillin/streptomycin (Sigma, St. Louis, Mo.).

Animals and Tumor Model: Inbred C57BL/6N female mice, (C57 mice) seven to eight weeks of age, were obtained from Simonsen Laboratories Inc. (Gilroy, Calif.). The right flanks of the mice were shaved and depiled the day prior to tumor inoculation. B16F10 cells ($5\times10^5$ cells in 0.05 mL PBS) were injected subcutaneously into the right hind flanks. Tumor size, i.e., length (l), width (w), and height (h), was measured 3 times a week with a vernier caliper. Tumor volumes were calculated using the formula for a hemiellipsoid (Rockwell and Kallman, 1972):

$$V = p/6 \times (l) \times (w) \times (h)$$

Biodistribution studies were performed on tumors having surface diameters of between about 5.5–7 mm and a depth of 4–6 mm.

Tissue Extraction Procedure: LuT2BET was administered via tail-vein injection at 10 or 20 µmol/kg. Tissues and plasma were analyzed at 3, 5 or 24 h post administration of the photosensitizer. Blood was collected in tubes containing 5 mg of solid EDTA and erythrocytes were removed by centrifugation. Plasma samples (125 µL) were mixed with 10 mM TRITON X-100® and analyzed for texaphyrin content by fluorescence. Weighed tissue samples were frozen in liquid nitrogen, and pulverized using a stainless-steel pulverizer chilled to −40° C. The powdered material was homogenized,(POLYTRON®, Brinkman) in 1.6 mL phosphate buffer (50 mM, pH 8.0). These homogenates were then mixed thoroughly with 3.0 mL methanol, and chloroform (3.0 mL) was added. After vigorous shaking on a Thomas Shaking Apparatus (Arthur H. Thomas, Philadelphia, Pa.), the phases were separated by centrifugation (10,000×g, 10 min, room temperature). The chloroform-rich bottom phase was carefully removed and brought to a volume of 3 mL with methanol. Samples were then analyzed for lutetium texaphyrin content by fluorescence (excitation=450 nm, emission=700–800 nm). Recovery of texaphyrin was >90%. Texaphyrin accumulation is expressed as µg drug/g tissue (wet weight) or per mL plasma.

Statistical analysis: Values are expressed as mean±SD. Values were compared using the unpaired Student's t-test. In the longevity analysis, Kaplan-Meier survival curves and log rank analysis for statistical significance were used. Statistical significance was assumed if $P<0.05$.

The distribution of LuT2BET in tissues and plasma of B16 melanoma bearing C57 mice at 3 h, 5 h, and 24 h following a 10 µmol/kg intravenous injection; and at 5 h, and 24 h following a 20 µmol/kg intravenous injection of the texaphyrin is shown in Table C.

TABLE C

Biodistribution of LuT2BET in B16 melanoma-bearing mice[1]

| LuT2BET (µmol/kg) | Time (h) | Plasma | Tumor | Muscle | Liver | Skin |
|---|---|---|---|---|---|---|
| 0 | 0 | 0 | 0 | 0 | 0 | 0 |
| 10 | 3 | 8.93 ± 1.0 | 11.27 ± 3.7 | 1.31 ± 0.4 | 94.20 ± 11.6[2] | 5.9 ± 1.25 |
| 10 | 5 | 1.22 ± 0.18 | 11.43 ± 1.08 | 0.76 ± 0.15 | 61.59 ± 8.31[2] | 3.80 ± 1.07 |
| 10 | 24 | 0 | 6.12 ± 1.77 | 0.60 ± 0.16 | 38.33 ± 6.0[2] | 2.99 ± 0.22 |
| 20 | 5 | 2.65 ± 0.87 | 21.44 ± 10.32 | 1.40 ± 0.48 | 103.48 ± 13.66[2] | 7.02 ± 0.70 |
| 20 | 24 | 0 | 3.40 ± 01.3 | 1.15 ± 0.48 | 65.59 ± 6.39[2] | 5.22 ± 1.11 |

[1]The lutetium texaphyrin distribution is expressed as µg/g tissue (wet weight) or µg/mL for plasma. These values represent the mean ± SD of five animals.
[2]An intrinsic fluorescence of 0.32 observed in the absence of lutetuum texaphyrin was subtracted from this value.

The data of Table C show that the control group (no texaphyrin) showed only minimal intrinsic fluorescence in the liver; all other tissues were void of material which would fluoresce in the 700–800 nm range after being excited by 450 nm light. Tumor levels of the texaphyrin were higher than plasma, muscle and skin at all three time points. The 20 µmol/kg dose produced greater tissue concentrations compared to the 10 µmol/kg dose, with the exception of the tumor levels at 24 h.

The texaphyrin exhibited good tumor localizing capacity as shown in Table C. The tumor:muscle ratios, for the 10 µmol/kg dose, were 8.6:1, 15:1, and 10.1:1 for 3 h, 5 h, and 24 h post injection, respectively. The 20 µmol/kg dose yielded ratios of 15.3:1 and 2.4:1, respectively. Some texaphyrin was retained in the skin; melanoma to normal skin ratios were between 0.5–3 to 1. High concentrations were found in the liver showing that the texaphyrin is not exclusively retained by the tumor. However, no toxicity was observed in this study.

A comparison with pharmacological data obtained using radiolabeled [$^{14}$C]-LuT2BET in SMT-F bearing mice showed significant but less selectivity. A dose of 8.64 µmol/kg LuT2BET produced drug uptake values of 5.1 µg/g, 4.7 µg/g, and 2.8 µg/g at 3 h, 5 h, and 24 h after injection, yielding tumor:muscle ratios of 8.45:1, 10:1 and 7:1, respectively. Therefore, increased uptake of lutetium texaphyrin into B16 melanoma was observed compared to the carcinoma SMT-F.

EXAMPLE 3

In vivo Detection of Melanin or a Melanin Metabolite Using Texaphyrin

The present example provides methods for detecting melanin or a melanin metabolite in vivo using texaphyrin. A texaphyrin or a texaphyrin metal complex is administered to a patient to be tested. Due to affinity of texaphyrin for melanin and melanin metabolites, texaphyrin would label those compounds. A detecting method such as fluorescent, magnetic, OCT, or x-ray based imaging methods, or, in the case of lymphatic mapping, lymphoscintigraphy or fluorescence would then be used to detect the texaphyrin. Detection would determine the location of the tumor, the amount of tumor burden, and/or the likelihood of metastatic disease.

For detection of metastasis to a lymph node, lymphatic mapping would be carried out. A detectable texaphyrin is injected intradermally around the site of a primary melanoma.

If the primary melanoma has already been removed, the intradermal injection is made into either side of the excision scar. It is important that injection of the texaphyrin is intradermal as subcutaneous injection will result in passage of the dye into the deeper lymphatic channels along the veins, bypassing the nodes that drain the dermal plexus.

The injection site is gently massaged to encourage passage of the dye along the lymphatics. When the injection is complete, an incision is made over the lymph basin that is the site of the expected lymphatic drainage. The skin flap closest to the primary melanoma is then dissected free from the underlying tissue and lymphatic channels, taking care to remain superficial to the lymphatic channels. When a texaphyrin-containing lymphatic channel is identified, it is followed through the fatty subcutaneous tissue to the first lymph node, i.e., the sentinel node, which is tested for presence of the detectable texaphyrin. If the lymph node is positive for the presence of texaphyrin, metastasis of the melanoma has occurred. In some patients, there can be more than one sentinel node. Radical lymphadenectomy can be performed as a separate procedure if the sentinel node is positive.

EXAMPLE 4

In vitro Detection of Melanin or a Melanin Metabolite Using Texaphyrin

The present example provides methods for detecting melanin or a melanin metabolite in vitro using texaphyrin. The in vitro sample is contacted with texaphyrin for a time sufficient to allow binding of texaphyrin to melanin or a melanin metabolite. A separation method such as anion or cation exchange chromatography, HPLC, or other separation means may be employed to remove unbound texaphyrin from texaphyrin bound to melanin or to a melanin metabolite. Mononuclear cells may be separated from a blood sample removed from a patient having been administered texaphyrin by PERCOLL™ (Pharmacia, Piscataway, N.J.) centrifugation, magnetic cell separation, or flow cytometry, for example. Alternatively, texaphyrin may be added to the blood sample, and the same separation techniques employed. An assay system may include directly measuring fluorescence of the bound texaphyrin and comparing the results with control values (assays lacking melanin and, separately, lacking texaphyrin) and with standard curves for melanin or a melanin metabolite. A further assay system may employ a detectable texaphyrin such as a radiolabelled texaphyrin, detecting the texaphyrin, and comparing results with control values.

One of skill in the art would be able to carry out further assays in light of the present disclosure, such as, for example, competitive assays.

The methods disclosed and claimed herein can be executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for determining presence of melanin or a melanin metabolite in a test subject comprising:

contacting a pharmaceutically effective amount of a texaphyrin with a urine, blood, or plasma test sample from the test subject; and determining binding of the texaphyrin with melanin or the melanin metabolite;

wherein binding demonstrates presence of melanin or the melanin metabolite in the test subject.

2. The method of claim 1 wherein the melanin metabolite is dihydroxyphenylalanine, a dihydroxyphenylalanine derivative, 5-S-cysteinyldopa, a methylated 5,6-dihydroxyindole, a methylated 5,6-dihydroxyindole-2-carboxylic acid, 6-hydroxy-5-methoxyindole-2-carboxylic acid, or 5-hydroxy-6-methoxyindole-2-carboxylic acid.

3. The method of claim 1 where the texaphyrin is fluorescent and determining binding is by observing fluorescent of the bound texaphyrin.

4. The method of claim 3 where the fluorescent texaphyrin is in a metal complex with Y(III), Lu(III), or Gd(III).

5. The method of claim 3 where observing fluorescence is by using excitation light having a wavelength of about 400–500 nm.

6. The method of claim 3 where observing fluorescence is by using excitation light having a wavelength of about 700–800 nm.

7. The method of claim 1 wherein the texaphyrin is selected from the group consisting of texaphyrins A1–A89 of Tables A and B.

8. The method of claim 1 where determining binding is by x-ray imaging, Raman scattering, optical coherence tomography, reflectance, or by magnetometry of the bound texaphyrin.

9. A method for determining presence of melanin or a melanin metabolite in a test subject comprising:

contacting a pharmaceutically effective amount of a texaphyrin represented by structure I with a sample of urine, blood, tissue, serum or plasma from the test subject; and determining binding of the texaphyrin with melanin or the melanin metabolite;

wherein binding demonstrates presence of melanin or the melanin metabolite in the test subject:

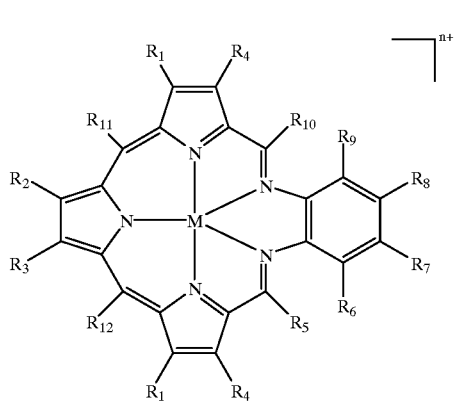

wherein

M is a divalent metal cation, or a trivalent metal cation;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, or aminoalkyl;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, or aminoalkyl; and n is an integer value less than or equal to 5.

10. The method of claim 9 wherein M is a divalent metal cation, and the divalent metal cation is Ca(II), Mn(II), Co(II), Ni(II), Zn(II), Cd(II), Hg(II), Fe(II), Sm(II), or UO$_2$(II).

11. The method of claim 9 wherein M is a trivalent metal cation, and the trivalent metal cation is Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), or U(III).

12. The method of claim 9 wherein M is a trivalent metal cation, and the trivalent metal cation is Lu(III) or Gd(III).

13. The method of claim 9 wherein $R_1$ is CH$_2$(CH$_2$)$_2$OH, $R_2$ and $R_3$ are CH$_2$CH$_3$, $R_4$ is CH$_3$, $R_7$ and $R_8$ are O(CH$_2$CH$_2$O)$_3$CH$_3$, and $R_5$, $R_6$, and $R_9$–$R_{12}$ are H.

14. A method for determining presence of melanin or a melanin metabolite in a test subject comprising:

contacting a pharmaceutically effective amount of a texaphyrin having structure II with the test subject; and determining binding of the texaphyrin with melanin or the melanin metabolite;

wherein binding demonstrates presence of melanin or the melanin metabolite in the test subject:

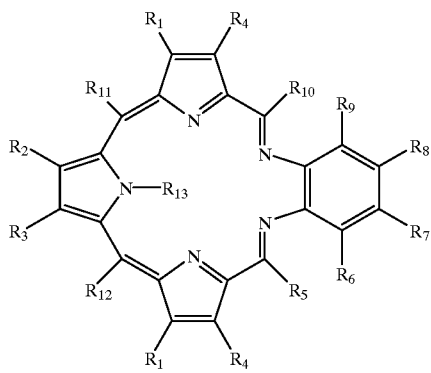

II

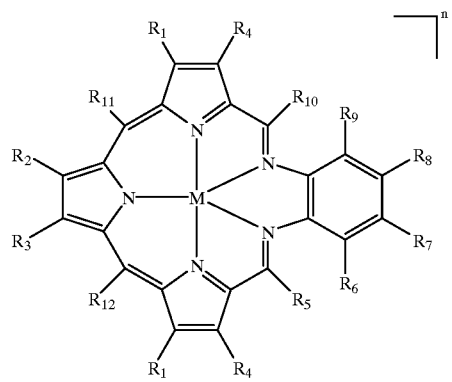

I wherein $R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, or aminoalkyl;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, or aminoalkyl; and $R_{13}$ is alkyl, alkenyl, oxyalkyl, or hydroxyalkyl having up to about 3 carbon atoms and having rotational flexibility around a first-bound carbon atom.

15. A method for determining abnormal presence of melanin or a melanin metabolite in a test subject comprising:

contacting a pharmaceutically effective amount of a texaphyrin with a body sample selected from the group consisting essentially of urine, blood, tissue, serum or plasma from the test subject;

contacting a pharmaceutically effective amount of a texaphyrin with a normal control sample; and determining binding of the texaphyrin with melanin or a melanin metabolite in the body sample from the test subject, and the control sample;

wherein when binding in the body sample from the test subject is greater than binding in the normal control sample, an abnormal presence of melanin or a melanin metabolite is present in the test subject.

16. A method for determining presence of melanin or a melanin metabolite in a urine, blood, or plasma sample from a test subject comprising:

obtaining the urine, blood, plasma, or tissue sample from the test subject;

contacting a pharmaceutically effective amount of a texaphyrin having structure I with the sample; and determining binding of the texaphyrin with melanin or the melanin metabolite;

wherein binding demonstrates presence of melanin or the melanin metabolite in the test subject:

wherein

M is a divalent metal cation, or a trivalent metal cation;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, or aminoalkyl;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, or aminoalkyl; and n is an integer value less than or equal to 5.

17. A method for diagnosing melanotic melanoma in a patient comprising:

administering a pharmaceutically effective amount of a texaphyrin to the patient;

obtaining a urine, blood, plasma, or tissue test sample from the patient; and determining binding of the texaphyrin with melanin or the melanin metabolite in the test sample;

wherein when binding of the texaphyrin in the test sample is greater than binding of texaphyrin in a control sample, melanotic melanoma is diagnosed in the patient.

18. A method for diagnosing melanotic melanoma in a patient comprising:

obtaining a urine, blood, plasma, or tissue test sample from the patient;

contacting the test sample and a control sample with a pharmaceutically effective amount of a texaphyrin; and determining binding of the texaphyrin with melanin or the melanin metabolite in the test sample, and in the control sample;

wherein when binding of the texaphyrin in the test sample is greater than binding of texaphyrin in the control sample, melanotic melanoma is diagnosed in the patient.

* * * * *

UNITED STATES PATENT AND TRADEMARK OFFICE
CERTIFICATE OF CORRECTION

PATENT : 6,022,526

DATED : February 8, 2000

INVENTOR(S) : Woodburn, *et al.*

It is certified that error appears in the above-identified patent and that said Letters Patent is hereby corrected as shown below:

In Claim 3, column 25, line 36, delete the word "where" and substitute --wherein--, therefor.

In Claim 3, column 25, line 38, delete the word "fluorescent" and substitute --fluorescence--, therefor.

UNITED STATES PATENT AND TRADEMARK OFFICE
CERTIFICATE OF CORRECTION

PATENT : 6,022,526
DATED : February 8, 2000
INVENTOR(S): Woodburn et al

It is certified that error appears in the above-identified patent and that said Letters Patent is hereby corrected as shown below:

In Claim 9, column 26, lines 1-17, delete the structure and substitute --

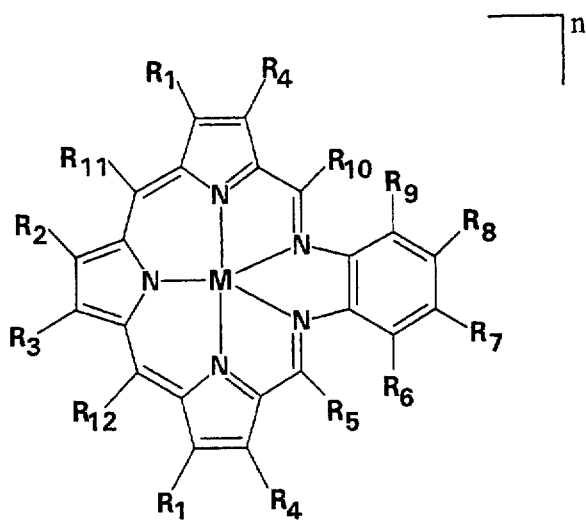

--, therefor.

Signed and Sealed this

Fifteenth Day of May, 2001

Attest:

NICHOLAS P. GODICI

Attesting Officer

Acting Director of the United States Patent and Trademark Office